(12) United States Patent
Lin et al.

(10) Patent No.: US 12,366,563 B2
(45) Date of Patent: Jul. 22, 2025

(54) SYSTEM AND METHOD FOR MONITORING AND DETECTING PATHOGENS

(71) Applicant: Hamilton Sundstrand Corporation, Charlotte, NC (US)

(72) Inventors: Fu Lin, Glastonbury, CT (US); Russell Taylor, Rockfall, CT (US); Daniel A. Mosher, Glastonbury, CT (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 853 days.

(21) Appl. No.: 17/373,560

(22) Filed: Jul. 12, 2021

(65) Prior Publication Data

US 2023/0011212 A1    Jan. 12, 2023

(51) Int. Cl.
*B01D 53/02*    (2006.01)
*G01N 33/00*    (2006.01)

(52) U.S. Cl.
CPC .................. *G01N 33/0004* (2013.01)

(58) Field of Classification Search
CPC .................................... B01N 33/0004
See application file for complete search history.

(56) References Cited

U.S. PATENT DOCUMENTS

| | | | |
|---|---|---|---|
| 6,241,950 B1 | 6/2001 | Veelenturf et al. | |
| 8,147,302 B2 | 4/2012 | Desrochers et al. | |
| 9,964,470 B2 | 5/2018 | Sharp | |
| 10,563,886 B2 | 2/2020 | McCormick et al. | |
| 2006/0071803 A1* | 4/2006 | Hamburger | G01N 21/53 702/29 |
| 2008/0182506 A1 | 7/2008 | Jackson et al. | |
| 2009/0194420 A1* | 8/2009 | Mariella, Jr. | B01L 3/502761 210/243 |
| 2013/0260668 A1 | 10/2013 | Stakutis et al. | |
| 2017/0081707 A1* | 3/2017 | Dillon | C12Q 1/689 |
| 2021/0404693 A1* | 12/2021 | Maheshwari | F24F 8/108 |
| 2022/0195536 A1* | 6/2022 | Molyneux | G01N 33/497 |
| 2023/0011212 A1* | 1/2023 | Lin | F24F 11/74 |

FOREIGN PATENT DOCUMENTS

JP    H08219507 A    *    8/1996

OTHER PUBLICATIONS

Translation of JP-H08219507-A (Year: 1996).*
European Search Report for Application No. 22184424.4, mailed Nov. 23, 2022, 11 pages.

* cited by examiner

*Primary Examiner* — Christopher P Jones
(74) *Attorney, Agent, or Firm* — CANTOR COLBURN LLP

(57) ABSTRACT

A method of identifying a location of pathogens in a structure including monitoring air within the structure for pathogens to set a baseline level, detecting a rise in pathogen density with respect to the baseline level, at least partially closing at least a first zone of the system, monitoring air from a second zone for a change in relative pathogen density to the previously detected pathogen density, and toggling the first zone and the second zone based on the change in relative pathogen density.

12 Claims, 2 Drawing Sheets

FIG. 2

Monitoring air within the structure for pathogens to set a baseline level

Detecting a rise in pathogen density with respect to the baseline level

At least partially closing at least a first zone of the system;

Monitoring air from a second zone for a change in relative pathogen density to the previously detected pathogen density Toggling the first zone and the second zone based on the change in relative pathogen density.

SYSTEM AND METHOD FOR MONITORING AND DETECTING PATHOGENS

BACKGROUND

Technological Field

The present disclosure relates generally to a system for monitoring building air quality, and more particularly to a system and method for detecting pathogens within the building.

Description of Related Art

Identifying the location of a biological hazard in large commercial buildings is critical in protecting the tenants' health and safety. In these buildings, an air-handling-unit (AHU) typically serves a dozen of variable-air-volume (VAV) boxes, each of which controls the airflow rate to individual rooms. To protect such buildings a sensor could be placed in every room and its readings checked on a regular basis. This would become very costly and economically prohibitive. Such a method would be satisfactory for specialized applications. However, there is clearly a need in the art for improved monitoring of buildings and air systems to promote broader implementation associated with high cost. The present disclosure provides a solution for this need.

SUMMARY OF THE INVENTION

A method of identifying a location of pathogens in a structure, such as a building, includes monitoring air within the structure for pathogens to set a baseline level, detecting a rise in pathogen density with respect to the baseline level, at least partially closing at least a first zone of the system, monitoring air from a second zone for a change in relative pathogen density to the previously detected pathogen density, and toggling the first zone and the second zone based on the change in relative pathogen density. The air can be circulated through the structure comprising multiple zones, rooms, and floors. The pathogen includes airborne pathogens, powders, or aerosols. The method can further include re-opening a first subset of the first zone and closing the second zone if the relative pathogen density decreased, and closing a portion of the first subset of the first zone and progressively closing an open subset of the first zone to identify a source of the pathogen.

The air can be circulated to the first zone and the second zone is by a single air handling unit and air access to each zone is controlled by a respective variable-air-volume box. The first zone and the second zone are not required to have the same volume. The method only requires to be monitored by a single sensor per air handling unit, where the sensor is placed at a return-air location. The method is controlled by an algorithm configured to toggle the zones open and closed.

A method of increasing detectability of a pathogen within a structure is also disclosed. The method includes monitoring air within the structure for pathogens to set a baseline level, and toggling at least a first zone and a second zone based on the change in relative pathogen density. The first zone and the second zone can then be continuously opened and closed on a schedule. The method can include closing a larger subset of the first zone or the second zone when detecting a rise in pathogen density with respect to the baseline level.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIG. 2 shows a block schematic for a method of controlling the system of FIG. 1.

DETAILED DESCRIPTION

Figure 1:
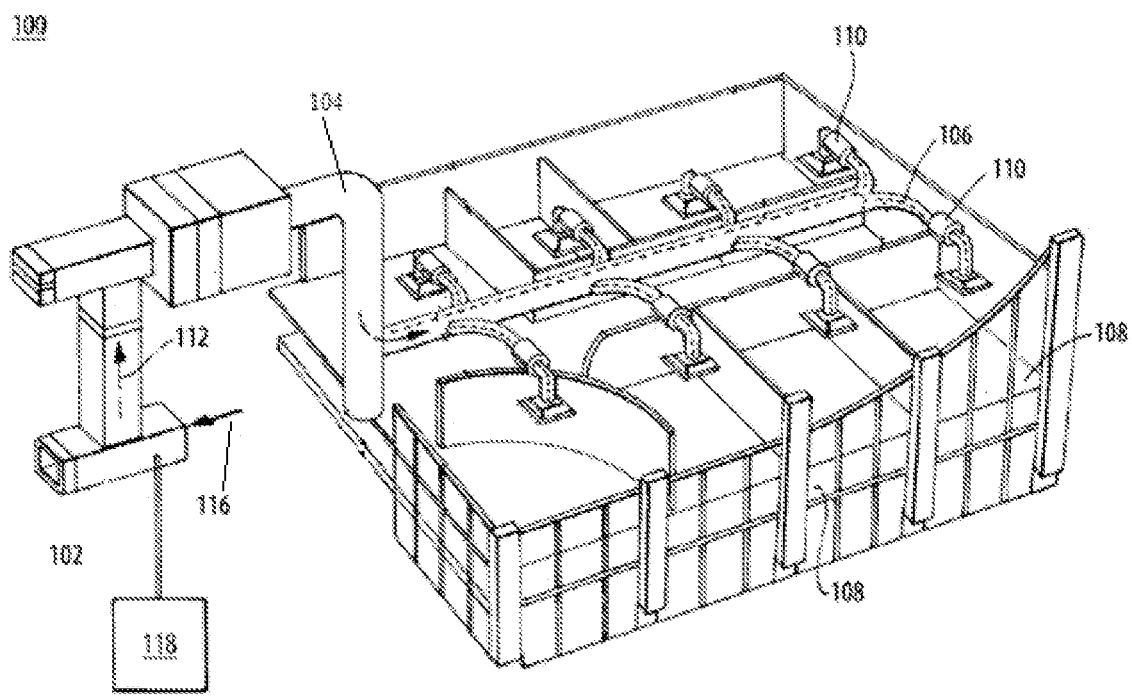
FIG. 1 shows a schematic view of an air handling system according to the disclosure.

Reference will now be made to the drawings wherein like reference numerals identify similar structural features or aspects of the subject disclosure. For purposes of explanation and illustration, and not limitation, a partial view of an exemplary embodiment of a system for detecting airborne pathogens within a building in accordance with the disclosure is shown in FIG. 1 and is designated generally by reference character 100, and FIG. 2 shows a block schematic for a method of controlling the system of FIG. 1. The detection system can be used to identify the location of the bio hazard or pathogen in the multi-zone scenario using only one sensor.

The system for detecting airborne pathogens in a building includes an air handling unit 102 for cycling the air throughout the system, a duct 104 attached to the air handling unit 102, wherein legs 106 of the duct 104 are connected to individual rooms 108, an air valve 110 corresponding to each of the plurality of the legs 106, and a bio sensor coupled to the return duct configured to detect the presence of airborne pathogens. A single duct 104 can be used to supply air to all floors but, it is considered that each floor can be controlled by independent ducts 104. The air valves 110 are controlled by a controller 118. The return air 116 is shown as returning in one large duct but includes a duct system similar to what is shown for the supply duct system with each room having an individual leg leading therefrom into a return air duct 116.

The system is used in one of two ways. The first being to identify a location of pathogens in the building. The identification is done by a constant monitoring of the air within the building for pathogens, airborne pathogens, powders, or aerosols in order to set a baseline level. If the monitor detects a rise in pathogen density with respect to the previously set baseline level, the controller will command at least partially closing a first zone of the system. The system is divided into multiple zones, each of which can be different sizes, and each zone can include a plurality of rooms, where the air supply to each room is controlled by a single air valve. As a portion of the system is closed off, the controller monitors air from the second zone for a change in relative pathogen density to the previously detected pathogen density. Based on the results of the second monitoring step the controller toggles the first zone and the second zone air valves. If the density increases, this means that the pathogen source is within the second zone. Thus, all valves in the first zone stay closed, and a portion of the valves in the second zone now close, with the process repeating itself by sub dividing the open valves based on the change in relative pathogen density and re-opening closed valves if the relative pathogen density drops.

The system 100 is also used for increasing the likelihood of detecting a pathogen within a structure. This method includes monitoring air within the structure for pathogens to set a baseline level, and sequencing through opening and closing sets of rooms within the structure continuously on a schedule to identify a pathogen source. The method can include closing a larger subset of the first zone or the second zone when detecting a rise in pathogen density with respect to the baseline level.

A benefit of these methods is the ability to control the airflow rate to the selected zones and to observe the rise and fall of the measurement of the pathogen density in the bio sensor and to concentrate the level of pathogen at the sensor by reducing the amount of return air coming from the unaffected regions and thus reducing the dilution of the pathogen. The algorithm can be used to monitor buildings with multiple floors, zones, rooms, and air handling units. Further, another benefit is cost reduction. Since only one bio sensor is required, it results in the minimum cost for the sensor and for the wire required to operate and monitor the sensor. Also, the process is automated without a human checking the infected zones by walking around or constantly monitoring the air in each room individually. This reduces the exposure of bio hazard to the occupants and first responders. Also, the theoretical number of possible zones where the threat could be is reduced by half in every cycle.

The methods and systems of the present disclosure, as described above and shown in the drawings, provide for a system and method for quick and effective detection of pathogens in an air system. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method of identifying a location of pathogen source in a structure that is partitioned into a plurality of zones, each of the zones having a plurality of rooms, the method comprising:
    monitoring, by a controller via a bio sensor, air within the structure for pathogens to set a baseline pathogen density,
    wherein the bio sensor is located in a return duct of an air handling unit that is operationally coupled to the controller and cycles air through plurality of legs into respective ones of the plurality of rooms, and
    wherein each of the plurality of legs includes one of a plurality of zone air valves controlled by the controller, and each of the air zone valves is initially opened;
    detecting, by the controller from the monitoring of air in the return duct via the bio sensor, a rise in pathogen density with respect to the baseline pathogen density;
    consecutively toggling to close and reopen, by the controller, all of the zone air valves in each one of the plurality of zones to identify one zone of the plurality of zones that has a relatively higher pathogen density, and keeping closed each one of the plurality of zones valves corresponding to one or more zones of the plurality of zones having a relatively lower pathogen density; and
    consecutively toggling to close and reopen, by the controller, each one of the zone air valves in the one zone to identify one room of the plurality of rooms in the one zone that has a relatively higher pathogen density, to thereby identify a location of a pathogen source, and keeping closed each one of the plurality of zone air valves corresponding to one or more rooms of the plurality of rooms in the one zone with the relatively lower pathogen density.

2. The method of claim 1, wherein the pathogen includes airborne pathogens, powders, or aerosols.

3. The method of claim 1, wherein air flow to each zone is controlled by a respective variable-air-volume box.

4. The method of claim 1, further comprising re-opening a first subset of a first zone and closing second zone if the relative pathogen density decreased.

5. The method of claim 4, further comprising closing a second subset of the second zone if the relative pathogen density increased.

6. The method of claim 4, further comprising closing a portion of the first subset of the first zone and progressively dividing an open subset of the first zone to identify a source of the pathogen.

7. The method of claim 5, further comprising closing a portion of the first subset of the first zone and progressively dividing an open subset of the first zone to identify a source of the pathogen.

8. The method of claim 1, wherein the first zone and the second zone are not the same volume.

9. The method of claim 1, wherein the air is monitored by a single sensor.

10. The method of claim 9, wherein the sensor is placed at a return-air location.

11. The method of claim 1, wherein the method is controlled by an algorithm configured to toggle a respective one of the plurality of zone air valves to control air flowing through each one of the zones based on the change in relative pathogen density.

12. The method of claim 1, wherein each of the zones are part of a building.

* * * * *